US006985829B2

(12) United States Patent
Jacquez

(10) Patent No.: US 6,985,829 B2
(45) Date of Patent: *Jan. 10, 2006

(54) METHOD FOR MEASURING A DEGREE OF ASSOCIATION FOR DIMENSIONALLY REFERENCED DATA

(75) Inventor: Geoffrey M. Jacquez, Ann Arbor, MI (US)

(73) Assignee: Bio-Analytics, Inc., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/775,319

(22) Filed: Feb. 10, 2004

(65) Prior Publication Data

US 2004/0162703 A1 Aug. 19, 2004

Related U.S. Application Data

(63) Continuation of application No. 10/457,963, filed on Jun. 10, 2003, now Pat. No. 6,738,728, which is a continuation of application No. 10/184,411, filed on Jun. 27, 2002, now Pat. No. 6,704,686, which is a continuation of application No. 10/008,741, filed on Nov. 13, 2001, now Pat. No. 6,460,011, which is a continuation of application No. 09/155,302, filed as application No. PCT/US97/04766 on Mar. 26, 1997, now Pat. No. 6,360,184.

(60) Provisional application No. 60/014,249, filed on Mar. 28, 1996.

(51) Int. Cl.
*G06F 15/00* (2006.01)
*G01N 15/04* (2006.01)

(52) U.S. Cl. .................. 702/179; 702/181; 702/19; 702/22; 435/153

(58) Field of Classification Search .............. 702/179, 702/181, 19, 22; 435/153
See application file for complete search history.

(56) References Cited

U.S. PATENT DOCUMENTS

| 5,464,742 | A  | * | 11/1995 | Swift et al.  | 435/6   |
| 5,528,516 | A  | * | 6/1996  | Yemini et al. | 702/104 |
| 6,360,184 | B1 | * | 3/2002  | Jacquez       | 702/181 |
| 6,460,011 | B1 | * | 10/2002 | Jacquez       | 702/181 |
| 6,704,686 | B2 | * | 3/2004  | Jacquez       | 702/179 |
| 6,738,728 | B2 | * | 5/2004  | Jacquez       | 702/179 |

FOREIGN PATENT DOCUMENTS

EP  WO 9736164  * 10/1997

* cited by examiner

*Primary Examiner*—Kamini Shah
(74) *Attorney, Agent, or Firm*—Howard & Howard

(57) ABSTRACT

A method for measuring a degree of association (58) between, and for selectively creating a grouping (40) of, n plurality of spatially referenced physical events (22) of a predetermined physical characteristic. The method includes the steps of assembling n plurality of physical events (26), assembling a universe of possible sample locations (36), determining a reference distribution (54), determining a restricted distribution (56), and determining the degree of association (58) between the n plurality of physical events. Specifically, the physical events each have an indicia of location and a physical characteristic above a threshold. The step (54) of determining a reference distribution is conducted by calculating a test statistic (78) for each of n' plurality of random allocations (74) of the n plurality of physical events over the selected n plurality of sample locations. Further, the step (58) of determining a restricted distribution includes calculating the test statistic (82) for each of n" plurality of restricted random allocations (80) of the n plurality of physical events over the n plurality of sample locations (62).

6 Claims, 3 Drawing Sheets

METHOD FOR MEASURING A DEGREE OF ASSOCIATION FOR DIMENSIONALLY REFERENCED DATA

This application is a continuation of application Ser. No. 10/457,963, filed Jun. 10, 2003, now U.S. Pat. No. 6,738,728, which is a continuation of application Ser. No. 10/184,411, filed Jun. 27, 2002, now U.S. Pat. No. 6,704,686, which is a continuation of application Ser. No. 10/008,741, filed Nov. 13, 2001, now U.S. Pat. No. 6,460,011, which is a continuation of application Ser. No. 09/155,302, filed Feb. 8, 1999, now U.S. Pat. No. 6,360,184, which is the National Stage of PCT/US97/04766 filed Mar. 26, 1997, which claims priority to U.S. Provisional Patent Application Ser. No. 60/014,249 filed Mar. 28, 1996.

SPONSORSHIP

This invention was made with government support by the United States of America under Grant No. R43 CA65366 awarded by the National Cancer Institute. The United States government has certain rights in the invention.

BACKGROUND OF THE INVENTION

1. Technical Field

The present invention relates generally to a method for detecting statistically significant dimensional relationships between physical events and, more particularly, to a method and apparatus for measuring a degree of association between spatially referenced physical events in order to group these physical events when appropriate.

2. Discussion

It is difficult to overstate the importance of accurately measuring localized occurrences of a physical event such as, for example, disease outbreaks or unsafe pollution concentrations. Incorrectly identifying the existence of such an event can lead to unnecessarily alarming individuals in the "affected" area as well as to causing the expenditure of resources, monetary and otherwise, better allocated elsewhere. Potentially even more devastating is the failure to recognize the existence of a localized event as early as possible. Left unchecked, highly contagious diseases can spread to cause an epidemic while environmental conditions such as increased pollution levels can irrevocably damage fragile natural balances.

Physical events are often spatially or temporally related with localized occurrences referred to as clusters. In these instances, the ability to accurately determine the existence of localized occurrences of physical events depends in part upon the specificity of the spatial or temporal property of each event. Despite the need to accurately measure statistically significant clustering in a variety of contexts, currently available modeling techniques do not accurately reflect the location of each event and therefore too often lead to incorrect inferences. This problem is particularly troublesome in spatially referenced physical events having uncertain spatial locations.

Sources of location uncertainty arise in a variety of contexts. For example, uncertainty can arise in an epidemiologic context due to the anonymity commonly maintained during the reporting of health events, the uncertainty of exposure locations given the mobility of human activity, and the transient nature of many environmentally transmitted disease causing agents. Uncertainty is amplified by the recording of event locations based upon zip code zones, census tracts, or grid nodes. Location uncertainty is also prevalent in the analysis of other spatially referenced physical events such as in the environmental and physical sciences (e.g. biology, geology, and hydrology).

Randomization testing of recorded events is commonly used to infer whether a spatial pattern exists within the sample of spatially referenced physical events. In these tests, the statistical significance of the spatial pattern is generally evaluated through the use of actual or estimated sample locations. When the actual locations of the samples are uncertain, a model is used to approximate the locations of the samples. The most frequently used method for approximating the location of a sample is the centroid model which assigns the area centroid location to all cases or samples occurring within an area.

A particular disadvantage of using randomization tests based upon centroid approximations is that the approach does not consider the spatial distribution of the at-risk population. As a result, approximations based upon the centroid of an area rather than the distribution of the at-risk population create an unnecessarily and inaccurately small universe of possible sample locations. For example, in epidemiological analyses, the universe of sample locations for randomization is more properly related to the geographic distribution of the human population in general and, more particularly, to the distribution of individuals at risk for a particular disease.

Additionally, randomization tests are problematic for spatial data because currently used techniques assume that the sampling space consists of the locations at which the observations were made. That is, they erroneously assume that the universe of possible locations consist entirely and solely of the sample locations. However, in most situations, other locations in the study area could have been sampled. As a result, the sampling space for the spatial randomization test is incorrectly specified and the distributions generated during the test pertain only to the sample locations rather than the at-risk population within the study area. This incorrect approximation leads to detection errors and the potentially dire consequences associated therewith, whether the locations of the physical events are certain or uncertain.

Accordingly, it is an object of the present invention to provide a method for accurately determining the degree of association between physical events.

A further object of the present invention is to provide a method for accurately determining the degree of association between physical events having uncertain locations.

Another object of the present invention is to determine the degree of association between a plurality of spatially referenced physical events based upon an analysis of reference and restricted distributions of a test statistic.

Still another object of the present invention is to determine the relative degree of illness for a given area based upon a comparison of the degree of association between the physical events to a threshold value.

A further object of the present invention is to determine the degree of association between a plurality of spatially referenced physical events through the use of a location model that reflects the spatial distribution of an at-risk population.

SUMMARY OF THE INVENTION

The present invention provides a method for measuring a degree of association between, and for selectively creating a cluster of, n plurality of spatially referenced physical events of a predetermined physical characteristic. The method includes the steps of assembling n plurality of physical events, assembling a universe of possible sample locations, determining a reference distribution, determining a restricted distribution, and determining the degree of association between the n plurality of physical events. Specifically, the physical events each have an indicia of location and a physical characteristic above a threshold. The step of determining a reference distribution is conducted by calculating a test statistic for each of n' plurality of random allocations of the n plurality of physical events over the selected n plurality of sample locations. Further, the step of determining a restricted distribution includes calculating the test statistic for each of n" plurality of restricted random allocations of the n plurality of physical events over the n plurality of sample locations.

BRIEF DESCRIPTION OF THE DRAWINGS

Further objects, features and advantages of the present invention will become apparent to those skilled in the art from studying the following detailed description and the accompanying drawings, in which.

DETAILED DESCRIPTION OF THE PREFERRED EMBODIMENT

The following description of a preferred embodiment of the present invention is merely exemplary in nature and is not intended to unduly limit the scope of the claimed invention. Moreover, the following description, while depicting the invention for use with spatially referenced epidemiological events, is intended to adequately teach one skilled in the art to use the method and apparatus to measure a degree of association between spatially referenced physical events, particularly those events having uncertain locations, regardless of the underlying nature or characteristic of the event. Specifically, those skilled in the art will appreciate that the method and apparatus described and claimed herein is applicable to determine the degree of association for a variety of spatially referenced physical events including environmental events related to geology, hydrology, or pollution control.

Figure 1:
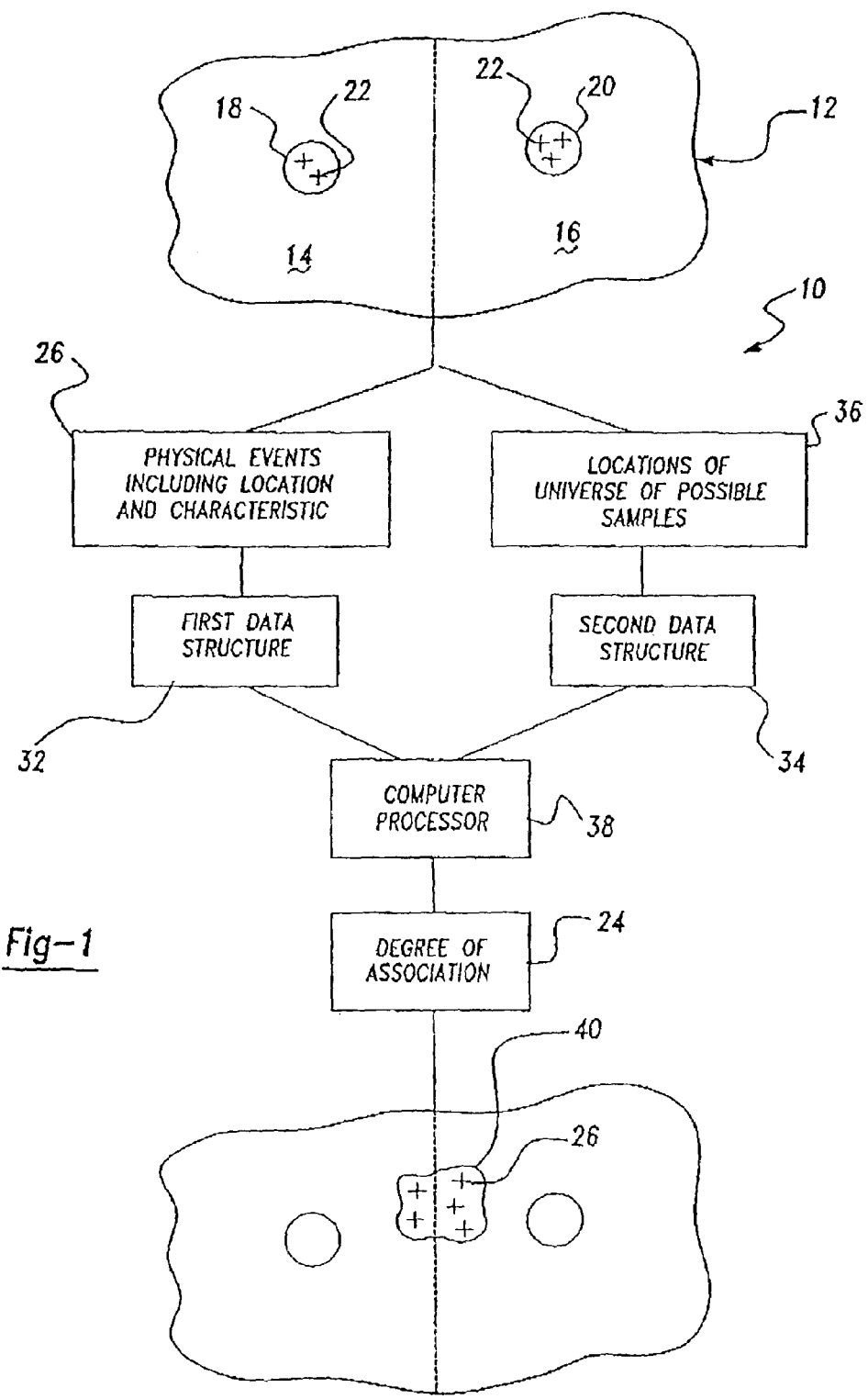
FIG. 1 is a schematic illustration of a method according to the present invention shown in relation to the physical events of interest.

FIG. 1 generally illustrates the implementation of the method and apparatus of the present invention 10 to a physical area 12 having a first sub-area 14 and a second sub-area 16. In this example, each of sub-areas 14 and 16 have a reporting station 18 and 20, respectively, where events of a physical characteristic are reported. The reporting of an epidemiological event to authorities, such as at a clinic, is commonly anonymous such that the residence of the person, presumably the best estimate of the location of contraction, is uncertain. This location uncertainty is represented in FIG. 1 by locating the event occurrences 22, identified by "+", within reporting stations 18 and 20. The method and apparatus 10 of the present invention includes assembling the physical events of interest and determining a degree of association that represents a measurement of the proximity of the event occurrences within the physical area 12. More particularly, in an embodiment of the invention, the degree of association for the physical events is used to group the events that warrant further investigation or an immediate response.

FIG. 1 further illustrates a structure for implementing the present invention as well as the relationship of this structure to physical area 12. The physical events 26, each including a physical characteristic and an associated, though uncertain, physical location, are selected and assembled in a first data structure 32. In a similar fashion, a second data structure 34 is assembled to include the physical locations of a universe of possible sample locations 36 that, in the embodiment of the invention hereinafter described, is a model of the actual at-risk population or the spatial density thereof. Computer processor 38 communicates with first and second data structures 32 and 34, respectively, to retrieve selected physical characteristics and possible sample locations therefrom and determine the degree of association 24 between the physical events in the manner described below with reference to FIG. 2. A grouping 40 of physical events 26 is created when the determined degree of association exceeds a predetermined value. In the context of this description, the creation of grouping 40 identifies the physical events that have a spatial proximity to one another that is sufficient to warrant further investigation or intervention.

With continued reference to FIG. 1, the physical events 26 included in first data structure 32 include only those events having a physical location within the area of analysis, e.g. area 22 of FIG. 1, and an associated physical characteristic above a predetermined threshold. It should be appreciated that the predetermined threshold may be zero whereby physical events exhibiting the desired physical characteristic are included in first data structure 32 regardless of the degree of the characteristic. Further, as to second data structure 34, the number of potential samples in the universe generally exceeds the number of physical events in first data structure 32. This excess of possible samples allows the method and apparatus of the present invention to more accurately determine the degree of association between the physical events as hereinafter described. Those skilled in the art will realize from this description that the location models hereinafter described may be used to expand the universe of samples and thereby increase the accuracy of the degree of association without regard to whether the physical events have a certain or uncertain location.

In sum, the present invention determines a degree of association between events that is representative of the actual association between the events. While the events have an actual degree of association based upon the proximity of the event locations, the actual association is incapable of measurement because the events are reported with locations that are generally not reflective of the actual event locations. The determined degree of association is used to selectively create an event grouping that warrants further investigation or intervention activity including action to mitigate or eliminate the condition represented by the physical characteristic of the reported event. As a result, the present invention modifies the location characteristics of the reported events to more accurately reflect actual conditions. The creation of an artificial group that more closely represents actual conditions is illustrated in FIG. 1 by grouping 40 compared to reporting locations 18 and 20.

It should be noted that while the descriptions and illustrations herein relate specifically to spatially referenced physical events occurring within an area, the invention is equally applicable to physical events associated with one another in other dimensions and occurring within a selected zone, e.g. temporal relationships within a time interval.

Figure 2:
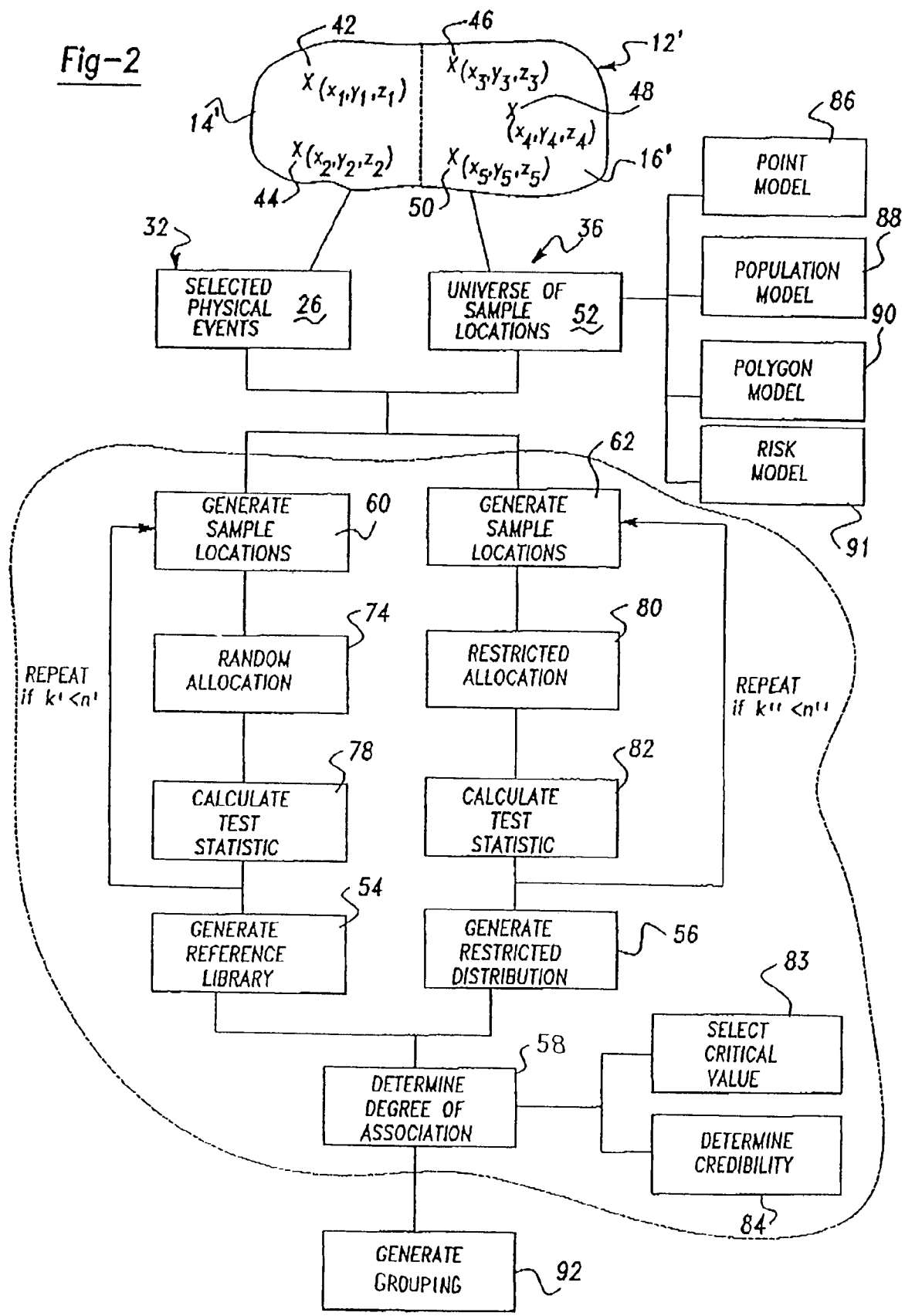
FIG. 2 is a flow chart showing steps of the preferred method with reference to a hypothetical spatial area of analysis.

FIG. 2 illustrates a specific exemplary application of the present invention with respect to an area of analysis 12' that includes a first sub-area 14' and a second sub-area 16' as previously described. In this example, each of the five selected physical events 26 illustrated in FIG. 1 are represented by an "x" and referenced by numerals 42, 44, 46, 48, and 50. Further, in this example, each of physical events 26 are further represented by data in the form $(x_i, y_i, z_i)$, where $x_i$ and $y_i$ are geographic coordinates representative of the location of the physical event and $z_i$ represents the physical characteristic of the event. While the locations of the physical events are illustrated as distributed within area of analysis 12', in the illustrated embodiment of the invention, the exact locations of the physical events are known only to the extent that events 42 and 44 occurred within first sub-area 14 and events 46, 48, and 50 occurred within second sub-area 16.

Selected physical events 42, 44, 46, 48, and 50 are assembled in first data structure 32 and a universe of sample locations 52 within area of analysis 12' are assembled within second data structure 36. In the present invention, universe 52 preferably includes the exact locations of the at-risk population within the respective sub-areas or the density distribution of the at-risk population within the area. While the preferred models for generating universe 52 are described in detail hereinafter, those skilled in the art will appreciate that universe 52 is based upon a measured or estimated distribution of a selected population as a whole, or a specified portion thereof.

Population density information is presently available from which the assembled sampling space or universe would include individuals particularly at risk to a certain health event. For example, the universe of sample locations may include the population density of individuals of a childhood age when determining the presence of statistically significant clustering of cases of childhood leukemia. Alternatively, the universe of possible sample locations could include the at-risk population density in view of the probability that an individual in the general population would be exposed to a condition conducive to contracting a particular disease.

FIG. 2 further schematically illustrates the steps performed, such as by computer processor 38 shown in FIG. 1, in determining the degree of association between physical events 42, 44, 46, 48, and 50. Specifically, the steps include generating a reference distribution 54, a restricted distribution 56, and determining a degree of association 58. The generation of reference and restricted distributions 54 and 56, respectively, include the step of generating sample locations 60 and 62, respectively, from the universe of possible sample locations in second data structure 34. The generated sample locations are equal in number to the physical events 26 included in first data structure 32. Those skilled in the art will appreciate from this description as well as the appended claims and drawings that virtually any number, n, of physical events 26 and sample locations may be selected for use with the present invention. However, in the preferred embodiment, the number, x, of possible sample locations within first sub-area 14' selected from second data structure 36 is equal to the number, x, of selected physical events 26 located in first sub-area 14'. Similarly, the number, y, of possible sample locations within second sub-area 16' selected from second data structure 36 is equal to the number, y, of selected physical events located in the second sub-area. Accordingly, in the illustrated embodiment shown in FIG. 2, each generation of sample locations 60 and 62 include two selected locations from first sub-area 14' and three selected sample locations from second sub-area 16'.

As generally indicated in FIG. 2, the generation of reference distribution 54 further includes randomly allocating, step 74, the physical characteristics $z_i$ of each selected physical event over all of the generated sample locations within area of analysis 12'. Specifically, each of the physical characteristics, i.e., $z_1, z_2, \ldots z_5$, are assigned with equal probability to each of the sample locations without regard to whether the sample locations are from the first or second subareas 14' and 16', respectively. This random allocation corresponds to a statistical null hypothesis of no association between the physical characteristics $z_i$ and their locations $(x_i, y_i)$ with in the respective sub-areas. A test statistic is then calculated in step 78 for each fully randomized allocation of the physical characteristics, $z_i$, over the repeatedly generated sample locations. In summary, reference distribution 54 is generated by repeatedly generating sample locations (step 60), randomly allocating the physical characteristics over the sample locations (step 74), and calculating the test statistic (step 78). Those skilled in the art will appreciate that the number of repetitions, n', performed to generate reference distribution 54 is represented by index of randomization k', and is variable and dependent upon a number of factors including the number of selected physical events, i.e. events 42, 44, 46, 48, and 50, and the significance level one wishes to resolve.

In general, it is convenient to express the test statistic as a cross product (a Γ product) although this invention applies generally to all statistics calculated from spatially referenced data. More specifically, for spatially referenced data, the Γ product is:

$$\Gamma = A \otimes B = \sum_{i=1}^{N} \sum_{j=1}^{N} a_{ij} b_{ij} \tag{1}$$

where "N" is the number of locations, "a" is a proximity measure and "b" is calculated from the observations on z.

Those skilled in the art will recognize that the null hypothesis for this cross-product statistic is that observations on z are independent of proximity. The alternative hypothesis being that observations on z are in some way associated with proximity.

There are three general measures of proximity that provide a ready means for quantifying spatial relationships in the Γ product. As is known in the art, these proximity measures quantify spatial and/or temporal relationships between pairs of points and are of three basic types: adjacency, distance, and nearest neighbor. Those skilled in the art will also appreciate the advantages and disadvantages of each of these three types as well as that each may be used in the method described and claimed herein. For exemplary purposes, adjacency based statistics such as join-count and Moran's I statistics may be used for adjacency based analysis whereas Mantel's test for distance-based and Cuzick and Edwards' test for nearest neighbor-based analysis may also be used. The equations for these analyses are generally recognized in the art. For completeness, Mantel's distance-based cross product statistic for space-time clustering is:

$$T = \sum_{i=1}^{n} \sum_{j=1}^{n} s_{ij} t_{ij} \qquad (2)$$

where $s_{ij}$ and $t_{ij}$ are space-time distances between cases i and j.

As shown in FIG. 2, spatially restricted distribution 56 is generated through restricted randomization, i.e., the physical characteristics, $z_i$, randomly allocated (step 80) among the sample locations within the same sub-area. For example, after generating an appropriate number of sample locations in step 62, characteristics $z_3$, $z_4$, and $z_5$ from physical events 46, 48, and 50 are allocated over the three sample locations within second sub-area 16'. Likewise, the $z_1$ and $z_2$ characteristics from events 42 and 44 are randomly allocated over the two selected sample locations within first sub-area 14'. By this restricted allocation, the association between the $z_i$ characteristics and the respective sub-areas for the physical events are maintained. The test statistic, Γ, is calculated in step 82 for each of the n" generations of sample locations thereby yielding the restricted distribution 56 of the test statistic. In a manner similar to reference distribution 54, the number, n", of repetitions used to calculate the test statistic for restricted distribution 56 is represented by index of restricted randomization k" and may vary depending upon, among other factors, the physical characteristics of interest. In one embodiment of the present invention the number of repetitions for the reference distribution, n', and number of repetitions for the restricted distribution, n", are equal.

Figure 3:
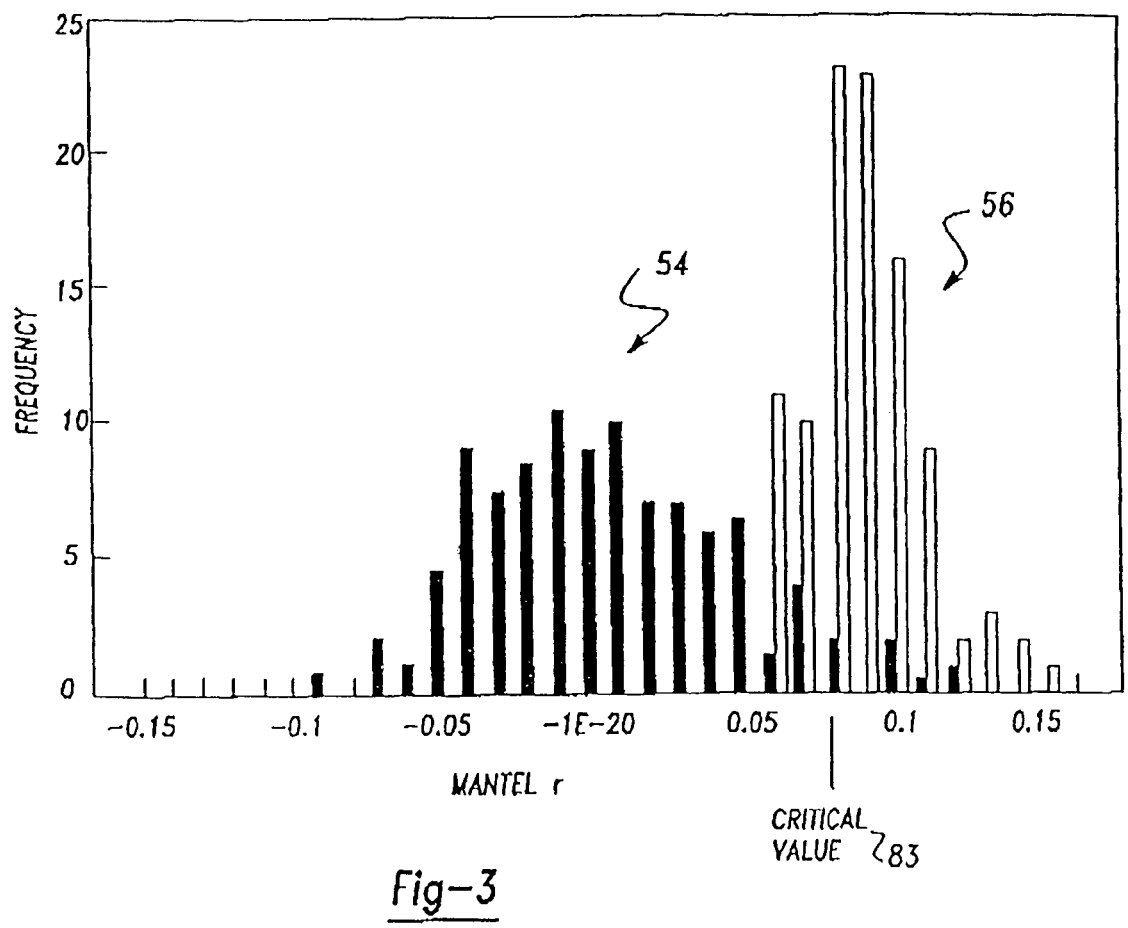
FIG. 3 is a graphic illustration of an exemplary reference distribution and restricted distribution of the Mantel test statistic.

A graphic illustration of reference distribution 54 and restricted distribution 56 is shown in FIG. 3. The relative positions of the distributions is the basis for determining the degree of association between physical events 26. More particularly, as shown in FIGS. 2 and 3, determination of the degree of association 58 includes selecting a critical value 83 and determining the credibility 84 of the null hypothesis. The selection of critical value 83 represents a trade off between the acceptability of receiving false positives, i.e. incorrectly rejecting the null hypothesis (type I error), and obtaining false negatives, i.e. accepting the null hypothesis when it is false (type II error). As a result, the selection of critical value 83 is dependent upon the particular event under scrutiny given the uncertain locations. For example, in an epidemiological context, a disease that is highly contagious or fatal generally deserves a high degree of scrutiny and therefore a low critical value is selected so that any suggestion of spatial association leads to the creation of an event group and further action or investigation. Conversely, if false positives have severe consequences, a higher critical value may be used. Critical value 83 is generally expressed as a 1−α value and is often approximately 95% (α=0.05).

Credibility 84 describes the possibility of statistically significant clustering and is defined as the proportion of the restricted distribution that meets or exceeds critical value 83. Credibility 84 represents the degree of association between physical events 26 and can be used to determine the statistical significance of the dimensional proximity of the events and whether the association warrants creation of a grouping 92 (FIG. 2). Specifically, if n plurality of physical events exhibit a credibility over a predetermined threshold, grouping 92 is created to encompass these events thereby indicating that the dimensional relationship between the physical events is statistically significant. In general, it is contemplated that a credibility of greater than 0.05 is statistically significant for most characteristics.

To this point, reference has been made to randomly sampling a universe of possible sample locations such as the at-risk population within an area in order to determine sample locations for the allocation of the physical characteristics. While a multitude of options are available to generate the sample space, four specific modeling alternatives are contemplated for use with the present invention. More particularly, the point model 86, population model 88, and polygon model 90 described in detail below and shown in FIG. 2 correspond to different levels of knowledge regarding spatial locations and are designed for situations commonly encountered in public health practice and the environmental sciences. Further, risk model 91 reflects not only the distribution of a general population but also the probability that the members of the population will contract a certain event of interest.

It will be apparent to one skilled in the art from the following description, that the accuracy of the information obtained from point model 86 is superior to that from the population and polygon models, while the population model provides the next best results. Further, for simplicity of exposition, the locations models are described below in the context of human population data. However, it should be appreciated that the models also apply in the earth sciences and other fields with little modification.

Point models 86 are used when a finite list of alternate exact locations are available. This situation arises, for example, when one knows a case occurred within a specific census district, but the exact place of residence of the case is not known. In point models, the list of alternate locations is constructed as the coordinates of all places of residence within the census district and can be obtained from a variety of methods including aerial photography, topographic maps showing building locations, and address-matching software which output latitude and longitude of street addresses. Point model 86 is preferred because it offers the greatest spatial resolution while its greatest weakness is that a list of alternative locations may be difficult to construct or be unavailable.

Population models 88 are used when the underlying population density distribution is known. This density distribution is then used to allocate possible case locations within an area. For example, locations with high population density are sampled most frequently. The resolution of the population model depends on the available population density surface generally obtainable such as from population density data produced by the Global Demography Project. Population data is also available from other sources such as U.S. census files that report population in census tracts and blocks as well as state information systems that report population by sections. Population model 88 offers ease of use due to the availability of the population density data as well as the ease of data incorporation into software applications. However, the population model may be less appropriate for diseases which strike particular risk groups whose population density is not highly correlated with the total population density within the area.

Polygon models 90 assume that the probability of sampling is uniform within sub-areas and applies when alternative places of residence are unknown, precluding the use of point models, and information on population density is lacking, thereby excluding population models. The use of a polygon model is frequently warranted due to data insufficiencies. However, these models offer the least resolution as a result of the assumption that population density is homogeneous within the sub-areas.

As described above, the point, population, and polygon models are point density functions describing the locations where events could have occurred. Risk model 91, on the other hand, recognizes that sampling probability at a location is dependent on two functions, i.e., the spatial density distribution of the physical events and the space-time process which propagates the physical characteristic of interest across the distribution. For example, for disease processes, the spatial density distribution of the physical events would generally describe the place of residence for individuals. Further, for a contagious disease, the second function would describe the transmission dynamics of the disease itself. Examples where the risk model would accurately represent the applicable universe of sampling locations include the study of malaria areas where small mosquito populations would have small sampling probability even in dense populations. As a further example, individuals proximate to a forested area would be given a higher probability of contracting lyme disease in view of the greater risk that they would come in contact with ticks. Further customization of the universe of possible sample locations may be provided in environmental applications such as pesticide exposures in agricultural areas, heavy metal transport, etc.

Various other advantages and modifications will become apparent to one skilled in the art after having the benefit of studying the teachings of the specification, the drawings, and the followings claims.

What is claimed is:

1. A method, comprising:
    establishing a set of occurrences of a physical event;
    determining a degree of association for each occurrence; and
    identifying a subset of the occurrences having a degree of association less than a predetermined value, wherein each occurrence includes an associated location and the degree of association represents a proximity between each occurrence and another occurrence.

2. A method, as set forth in claim 1, wherein the proximity is based on at least one reference location.

3. A method, as set forth in claim 2, the reference location being defined by a model of an at-risk population.

4. A method, as set forth in claim 3, the model representing the spatial-density of the at-risk population.

5. A method, comprising:
    establishing a set of occurrences of a physical event;
    determining a degree of association for each occurrence;
    identifying a subset of the occurrences having a degree of association less than a predetermined value, wherein each occurrence includes an associated location and each associated location is an estimate of the location of the occurrence; and,
    modifying the estimate of the location of the occurrence as a function of the degree of association.

6. A method, comprising:
    establishing a set of occurrences of a physical event;
    determining a degree of association for each occurrence; and
    identifying a subset of the occurrences having a degree of association less than a predetermined value, the physical event having a parameter, each occurrence having a value of the parameter;
    comparing the value of the parameter of each occurrence with a second predetermined value; and,
    including, in the subset, occurrences whose value of the parameter exceeds the second predetermined value.

* * * * *